United States Patent
Pomplun et al.

(10) Patent No.: US 6,530,910 B1
(45) Date of Patent: Mar. 11, 2003

(54) FLUSHABLE RELEASE FILM WITH COMBINATION WIPER

(75) Inventors: William S. Pomplun, Neenah, WI (US); Yihua Chang, Appleton, WI (US); John E. Kerins, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/131,021

(22) Filed: Aug. 7, 1998

Related U.S. Application Data
(60) Provisional application No. 60/070,258, filed on Dec. 31, 1997.

(51) Int. Cl.[7] .............................................. A61F 13/15
(52) U.S. Cl. ........................ 604/364; 604/365; 604/367; 604/390; 604/385.05; 428/40.1; 428/41.8
(58) Field of Search ........................... 604/369, 364, 604/365, 367, 390, 385.05; 428/40.1, 41.8

(56) References Cited

U.S. PATENT DOCUMENTS

| | | | | |
|---|---|---|---|---|
| 3,515,582 A | * | 6/1970 | Blackley ........................ 117/143 |
| 3,550,592 A | | 12/1970 | Bernardin ...................... 128/290 |
| 3,554,788 A | | 1/1971 | Fechillas ....................... 117/140 |
| 3,559,650 A | | 2/1971 | Larson .......................... 128/290 |
| 3,575,173 A | * | 4/1971 | Loyer ........................... 128/290 |
| 3,636,952 A | * | 1/1972 | George ......................... 128/287 |
| 3,654,064 A | * | 4/1972 | Laumann ...................... 161/156 |
| 3,654,928 A | * | 4/1972 | Dchane ........................ 128/290 |
| 3,692,725 A | * | 9/1972 | Duchane ...................... 260/29.6 |
| 3,702,610 A | * | 11/1972 | Sheppard et al. ............. 128/284 |
| 3,707,430 A | | 12/1972 | Costanza et al. ............. 161/123 |
| 3,756,232 A | * | 9/1973 | Noguchi et al. .............. 128/290 |
| 3,804,092 A | * | 4/1974 | Tunc ............................ 128/284 |
| 3,838,695 A | * | 10/1974 | Comerford et al. .......... 128/290 |
| 3,846,158 A | * | 11/1974 | Vasilyadis .................... 117/68.5 |
| 3,855,052 A | | 12/1974 | Mestetsky .................... 161/167 |
| 3,881,041 A | | 4/1975 | Glienke ........................ 428/40 |
| 3,881,487 A | * | 5/1975 | Schrading .................... 128/284 |
| 3,923,592 A | * | 12/1975 | George et al. ................ 162/168 |
| 3,939,836 A | * | 2/1976 | Tunc ............................ 128/284 |
| 3,952,745 A | * | 4/1976 | Duncan ........................ 128/287 |
| 4,023,570 A | * | 5/1977 | Chinai et al. ................. 128/290 |
| 4,097,943 A | | 7/1978 | O'Connell .................... 5/335 |
| 4,151,344 A | * | 4/1979 | Doss et al. ................... 528/34 |
| 4,171,397 A | * | 10/1979 | Morrow ....................... 428/195 |
| 4,186,233 A | | 1/1980 | Krajewski et al. ........... 428/213 |
| 4,229,239 A | | 10/1980 | Arai ............................. 156/155 |
| 4,269,650 A | | 5/1981 | Arai ............................. 156/540 |
| 4,282,054 A | * | 8/1981 | Mattor et al. ................. 156/289 |
| 4,333,464 A | | 6/1982 | Nakano ........................ 128/290 R |
| 4,348,293 A | | 9/1982 | Clarke et al. ................. 252/90 |
| 4,372,311 A | | 2/1983 | Potts ............................ 128/287 |
| 4,386,135 A | * | 5/1983 | Campbell et al. ............ 428/447 |
| 4,416,791 A | | 11/1983 | Haq ............................. 252/90 |
| 4,536,434 A | | 8/1985 | Magnotta ..................... 428/200 |
| 4,588,400 A | | 5/1986 | Ring et al. ................... 604/304 |
| 4,654,395 A | | 3/1987 | Schulz ......................... 526/318.42 |
| 4,655,868 A | | 4/1987 | Hefele .......................... 156/238 |
| 4,705,584 A | | 11/1987 | Lauchenauer ................ 156/79 |
| 4,731,143 A | | 3/1988 | Cross ........................... 156/231 |
| 4,900,554 A | | 2/1990 | Yanagibashi et al. ........ 424/448 |
| 4,959,264 A | | 9/1990 | Dunk et al. ................... 428/331 |
| 5,009,647 A | | 4/1991 | Cross et al. .................. 604/332 |
| 5,009,652 A | | 4/1991 | Morgan et al. ............... 604/289 |
| 5,041,252 A | * | 8/1991 | Fuji et al. ..................... 264/176.1 |
| 5,061,559 A | | 10/1991 | Ogusi et al. .................. 428/343 |
| 5,071,648 A | | 12/1991 | Rosenblatt ................... 424/78.06 |
| 5,082,706 A | | 1/1992 | Tangney ....................... 428/40 |
| 5,198,299 A | | 3/1993 | Kato et al. .................... 428/340 |
| 5,300,358 A | | 4/1994 | Evers ........................... 604/364 |
| 5,332,607 A | | 7/1994 | Nakamura et al. ........... 428/40 |
| 5,391,423 A | | 2/1995 | Wnuk et al. .................. 428/217 |
| 5,405,342 A | * | 4/1995 | Roessler et al. .............. 604/364 |
| 5,405,475 A | | 4/1995 | Kraft et al. ................... 156/275.5 |
| 5,458,591 A | * | 10/1995 | Roessler et al. .............. 604/364 |
| 5,468,807 A | | 11/1995 | Tsurutani et al. ............. 525/240 |

(List continued on next page.)

FOREIGN PATENT DOCUMENTS

| | | |
|---|---|---|
| EP | 0 461 484 | 12/1991 |
| EP | 0479404 | 4/1992 |
| JP | 63-46233 | 2/1988 |
| JP | 5-200375 | 8/1993 |
| JP | 5-228172 | 9/1993 |
| JP | 5-293070 | 11/1993 |
| JP | 7-70525 | 3/1995 |
| WO | 94/23769 | 10/1994 |
| WO | WO 96 20831 | 7/1996 |
| WO | WO 97 18082 | 5/1997 |
| WO | WO 99 08727 | 2/1999 |

OTHER PUBLICATIONS

Yetter et al. U.S. Statutory Invention Registration No. H1340 1994.
JP 06 100845, Apr. 12, 1994, Abstract.
JP 07 003699, Jan. 6, 1995, Abstract.
JP 06 126901, May 10, 1994, Abstract.
JP 06 134910, May 17, 1994, Abstract.

Primary Examiner—Weilun Lo
Assistant Examiner—Michael G. Bogart
(74) Attorney, Agent, or Firm—Kilpatrick Stockton LLP

(57) ABSTRACT

The present invention is directed to a flushable release liner/wiper combination. The flushable release liner/wiper combination is formed by applying a release coating onto a first surface of a water-sensitive film and an absorbent fibrous material onto an opposite surface of the water-sensitive film. The flushable release liner/wiper combination maintains its integrity and strength when in use, but loses its integrity and strength when placed in contact with water. The flushable release liner/wiper combination quickly breaks up and disperses in a flushing toilet or sink due to the force of the flowing water on the liner/wiper combination. Moreover, the present invention is directed to methods of making the flushable release liner/wiper combination and water-dispersible products, including flushable products, which contain the flushable release liner/wiper combination.

18 Claims, No Drawings

U.S. PATENT DOCUMENTS

| | | | |
|---|---|---|---|
| 5,472,518 A | 12/1995 | Patnode et al. | 134/34 |
| 5,476,457 A * | 12/1995 | Roessler et al. | 640/364 |
| 5,509,913 A | 4/1996 | Yeo | 604/364 |
| 5,529,830 A | 6/1996 | Dutta | 428/176 |
| 5,569,348 A | 10/1996 | Hefele | 156/239 |
| 5,578,344 A * | 11/1996 | Ahr et al. | 427/211 |
| 5,584,800 A | 12/1996 | Scholz et al. | 602/6 |
| 5,603,691 A | 2/1997 | Scholz et al. | 602/6 |
| 5,613,959 A * | 3/1997 | Roessler et al. | 604/364 |
| 5,691,022 A | 11/1997 | Knauf | 428/40.1 |
| 5,700,571 A | 12/1997 | Logue et al. | 428/352 |
| 5,716,685 A | 2/1998 | Kumar et al. | 428/40.1 |
| 5,981,012 A * | 11/1999 | Pomplun et al. | 128/41.8 |
| 5,985,396 A * | 11/1999 | Kerins et al. | 428/41.8 |
| 6,138,278 A * | 10/2000 | Taylor et al. | 2/114 |

\* cited by examiner

FLUSHABLE RELEASE FILM WITH COMBINATION WIPER

RELATED APPLICATIONS

The present nonprovisional application claims the benefit of priority to the corresponding provisional patent application No. 60/070,258, filed Dec. 31, 1997.

FIELD OF THE INVENTION

The present invention is directed to a flushable release liner/wiper combination. The flushable release liner/wiper combination is formed by applying a release coating onto at least one surface of a water-sensitive film and attaching a wiper to the opposite surface of the water-sensitive film. The flushable release liner/wiper combination maintains its structural integrity and strength when in use, but begins to disperse when placed in contact with water. When placed in a conventional sink or toilet, the flushable release liner/wiper combination quickly loses its integrity and strength and breaks up under the forces of flowing water. Moreover, the present invention is directed to products, including flushable and non-flushable products, which contain the flushable release liner/wiper combination.

BACKGROUND OF THE INVENTION

Disposable products have revolutionized modern lifestyle and are of great convenience to society. Such products generally are relatively inexpensive, sanitary and quick and easy to use. Disposal of such products, however, is a concern as landfills close and incineration contributes to urban smog and pollution. Consequently, there is an urgent need for disposable products that can be disposed of without dumping or incineration. An ideal disposal alternative would be the use of municipal sewage treatment plants and private residential septic systems. Products suited for disposal in sewage systems that can be flushed down a conventional toilet are termed "flushable." An essential feature of flushable products is that they must have sufficient strength for their intended use, yet lose structural integrity upon contact with water.

Numerous consumer products, which were formerly unable to be disposed of in a conventional toilet, are made flushable today. Such products include water-soluble films, wipers, tampon applicators, etc. However, many consumer products have remained unflushable.

One such product that has remained unflushable to date is release liners. Release liners are used to temporarily cover an adhesive layer before use in many personal care products. The release liner provides protection for the adhesive layer against exposure to materials, which might negatively affect the ability of the adhesive strip to adhere to a desired substrate, and provides protection against undesired, premature adhesion to a substrate. Conventional release liners comprise a paper substrate coated with a release coating. The release coating is formulated to provide very little adhesion of the coated paper to any other substrate, particularly pressure-sensitive, hot-melt adhesives, so the release liner may be easily removed from the adhesive strip without disturbing the adhesive strip. Typically, release coatings comprise a silicone-containing polymeric material.

Release liners are used in many personal care products. For example, many sanitary napkins have an adhesive strip on the backside of the napkin (the napkin surface opposite to the body-contacting surface) to fix the napkin to an undergarment and hold the napkin in place against the body. Before use, the adhesive strip is protected with a peelable release liner. Once removed, the peelable release liner must be discarded. Since conventional peelable release liners are typically silicone-coated paper, the release liners do not disperse in water; consequently, disposal options are limited to depositing the release liner in a trash receptacle. Although disposing of conventional release liners in a toilet would be convenient to the consumer, such improper disposal potentially creates blockages in the toilet or household sewer line.

Further, conventional peelable release liners, once removed from an adhesive strip, have very little utility. Consumers typically dispose of the release liner immediately after removal from the adhesive strip. Often a consumer wishes to wipe the perineal area of the body prior to using a new sanitary napkin. With conventional release liners, the consumer must resort to using a separate wiping product, such as bath tissue, to wipe the perineal area.

What is needed in the art is a low-cost flushable release liner/wiper combination, which can be discarded and then flushed in a conventional toilet. Such a flushable release liner/wiper combination would function as a release liner having additional utility as a wiper, eliminating the need to use a separate product to wipe the perineal area of the body prior to using a new sanitary napkin. Such a flushable release liner/wiper combination would offer convenience to the consumer, and not cause problems such as blockages in the sewage transport process.

SUMMARY OF THE INVENTION

The present invention is directed to a flushable release liner/wiper combination comprising a thin release coating on a first surface of a water-sensitive film and an absorbent wiper attached to a second surface of the water-sensitive film, which is opposite the first surface. The coated water-sensitive film/absorbent wiper combination functions like conventional release papers and wiping materials currently used. Conventional release papers comprise a peelable coated paper, which covers the adhesive strip on a feminine sanitary napkin. Unlike conventional release papers, the coated water-sensitive film/absorbent wiper combination of the present invention provides utility as a wiper and rapidly loses integrity and strength when discarded in a conventional toilet. Without the support of the water-sensitive film, the thin release coating and absorbent wiper material begin to break up under the force of flushing. The three-layer structure of the flushable release liner/wiper combination offers (1) the performance of a paper-based release liner with a wiping surface, (2) the additional option of disposal in a toilet, and (3) potentially lower cost.

The present invention is also directed to a method of preparing a flushable release liner/wiper combination. The method comprises coating a thin layer of polymer having release characteristics onto a base film, wherein the base film comprises a water-sensitive polymer. When dry, the resulting two-layer laminate displays mechanical features comparable to a conventional coated paper liner. The base film itself may be manufactured, taking into consideration variables such as film thickness, molecular weight, and blending additives, to control the functionality of the plastic film. The polymeric coating controls the release characteristics of the plastic film. The coating is formulated to provide very little adhesion to many substrates, particularly pressure-sensitive, hot-melt adhesives, so the coating may be easily removed from an adhesive strip without disturbing the adhesive strip, while having high adhesion to the water-sensitive film substrate. The coating formulation ensures that the two-layer polymer film peels at the surface of the release coating, not at the interface between the coating and the water-sensitive base film.

The coated water-sensitive film is further combined with an absorbent fibrous material such that the fibrous material provides a wiping surface on the film opposite to the release coating. The fibrous material may be attached to the film by any means known to those of ordinary skill in the art, desirably by extrusion lamination. The fibrous material, independent from the coated film, may be flushable/dispersible when placed in contact with water, such as found in a conventional sink or toilet.

The present invention is also directed to articles containing the flushable release liner/wiper combination. Specifically, the flushable release liner/wiper combination of the present invention is useful in connection with a variety of products, and especially absorbent products such as sanitary napkins, panty liners, diapers, dressings and the like. Although the release liner of the present invention finds particular use in the above-mentioned products, the concept of a flushable release liner/wiper combination has potential for any other application requiring a release material.

The present invention provides a mechanism for eliminating disposal problems associated with various consumer products. A nonlimiting detailed description of the invention and examples of specific embodiments are provided below.

DETAILED DESCRIPTION OF THE INVENTION

The present invention is directed to a flushable release liner/wiper combination comprising a thin release coating on a first surface of a water-sensitive film and an absorbent wiper on an opposite, second surface of the water-sensitive film. The coated water-sensitive film of the release liner/wiper combination functions like a conventional release paper. However, unlike conventional release papers, the coated water-sensitive film of the present invention is "flushable." As used herein, the term "flushable" describes a product which rapidly loses integrity and strength when discarded in a conventional sink or toilet, and breaks up under the force of flowing water such that the product may be transported by flowing water through a sewage system into a municipal sewage treatment plant or private residential septic system. Further, the flushable release liner/wiper combination also provides an absorbent wiping surface, unlike conventional release papers. The flushable feature of the release liner/wiper combination of the present invention comes from the water-sensitivity of the base film and the low strength of the thin release coating and the absorbent wiper material. When immersed in water, the exposed surfaces of the base film readily wet and weaken. The water-sensitive film quickly loses integrity and strength when exposed to water. When the film substrate loses its mechanical integrity, the release coating and the absorbent wiper material, which are thin and mechanically weak, begin to disperse under the flushing force of a toilet or the force of water flow in a sink.

The flushable release liner/wiper combination of the present invention is prepared by any single or multiple step process wherein a thin layer of "release material" is coated onto a first surface of a water-sensitive film and an absorbent fibrous material is attached to a second and opposite surface of the water-sensitive film. As used herein, the term "release material" describes a material which possesses release characteristics. In multiple step processes for forming the flushable release liner/wiper combination of the present invention, the order of the method steps is not important. For example, the water-sensitive film may be coated with a thin layer of release material and subsequently attached to the absorbent fibrous material. Alternatively, the water-sensitive film may be attached to the absorbent fibrous material and subsequently coated with a thin layer of release material. In single step processes for forming the flushable release liner/wiper combination of the present invention, the thin layer of release material, the water-sensitive film and the absorbent fibrous material are simultaneously laminated together.

The release material may be coated onto the water-sensitive film by any coating process known to those of ordinary skill in the art. Suitable processes for coating the release material onto the water-sensitive film include, but are not limited to, extrusion coating, solvent-base coating, and hot-melt coating. Suitable extrusion coating techniques include, but are not limited to, curtain extrusion coating and co-extrusion of the coating and the water-sensitive film. Suitable co-extrusion coating techniques include, but are not limited to, a cast chill roll process and a blown bubble extrusion process. Suitable solvent-base coating techniques include, but are not limited to, spray coating and screen printing. Suitable hot-melt coating techniques include, but are not limited to, slot coating, spray coating, screen printing and gravure coating. Desirably, the coating process for coating the release material onto the water-sensitive film is a hot-melt slot coating process or an extrusion coating process.

In one embodiment of the present invention, a continuous coating of release material is applied to the water-sensitive film by the following method. Molten release material is delivered from a melting tank through a heated hose to a slot die. The temperature of the melting tank, hose and slot die may vary depending upon the melt rheology of the release material in the coating process. The molten material is uniformly applied directly onto the water-sensitive film (direct coating), or alternatively, onto a carrier substrate and subsequently transferred onto the water-sensitive film (transfer coating). Line speeds may vary depending upon the "open time" of the release material. As used herein, the "open time" of a material refers to the amount of time required for the material to loose its tackiness. In a transfer coating process, the coated carrier substrate moves further through the process and comes into contact with the water-sensitive film, which is properly aligned with the coated carrier substrate. The coating is transferred from the carrier substrate to the water-sensitive film under pressure as the film and carrier substrate pass through a nip roll. In practice, optimum coating thickness is achieved by adjusting processing factors which include, but are not limited to, the release material, the coating temperature, the resin flow rate, line speed, and the pressure applied at the nip roll.

In a further embodiment of the present invention, a discontinuous coating of release material is applied to the water-sensitive film by the following method. Molten release material is delivered from a melting tank through a heated hose to a slot die located inside a screen cylinder. As in the above-described method, the temperature of the melting tank, hose and screen cylinder may vary depending upon the melt rheology of the release material in the coating process. The molten release material is distributed uniformly on the inner wall of the rotating screen cylinder, and then applied through screen holes, as a geometric pattern of discrete dots, directly onto the water-sensitive film (direct coating), or alternatively, onto a carrier substrate outside and adjacent to the screen cylinder (transfer coating). The screen and film/carrier substrate may move at the same or different speeds depending upon the distortion of dot shape desired. When the screen and film/carrier substrate travel at the same speed, symmetrical dots are produced. When the screen and film/carrier substrate travel at different speeds, dots elongated in the machine direction are produced. Line speed may vary depending upon the open time of the release material. In the transfer coating process, the dots spread out as a result of the nip pressure. The degree of spreading depends on the pressure, open time of the release material, and the coating speed. In practice, dot spacing may be controlled by adjusting processing factors which include, but are not limited to, the release material, the coating temperature, the screen pattern, the resin flow rate, screen speed, line speed, and the pressure applied at the nip roll.

It should be noted that the carrier substrate used in the above-described transfer coating processes may be any substrate which can transfer the release coating to the water-sensitive film. Suitable carrier substrates display little or no adhesion with the release coating relative to the adhesion between the water-sensitive film and the release coating. Suitable carrier substrates include, but are not limited to, release paper, release films, and release-coated substrates such as fabrics and/or belts. Desirably, the carrier substrate is a release paper. More desirably, the carrier substrate is an AKROSIL® High Release Paper.

In yet a further embodiment of the present invention, a coating of release material is co-extruded onto the water-sensitive film. In this process, molten release material is delivered from an extruder through a heated hose to an extrusion chamber. In a separate extruder, molten water-sensitive film material is delivered from the separate extruder through a second heated hose to an adjacent extrusion chamber. The release material and water-sensitive film material are allowed to come into contact with one another within the extrusion chamber and simultaneously extruded to form the coated film.

In any of the above-mentioned coating processes, the adhesion of the release coating to the water-sensitive film should be greater than the adhesion of the release coating to the screen (direct coating) or the carrier substrate (transfer coating). The choice of release material should take into consideration the desired release characteristics and adhesion properties of the release material. The release material should have good adhesion to the water-sensitive substrate. Suitable release materials for use in the present invention include any processible material with appropriate melt rheology, release characteristics and adhesion properties for application by the above-described coating processes. Suitable materials include, but are not limited to, water insoluble materials such as polyolefins, fluoropolymers and silicones, as well as, water-dispersible materials such as silicone esters, copolymers of silicone esters or blends of silicone-containing compounds.

One or more of the release materials above may be combined to form the release coating of the flushable release liner/wiper combination. Further, the release material may contain one or more of the following additives including, but not limited to, compatibilizers, processing aids, plasticizers, tackifiers, detackifiers, slip agents, and anti-microbial agents, as fabricating agents or as modifiers depending on the specific properties desired in the release coating and the final product. The release coating should be formulated to provide little adhesion to a variety of substrates, particularly pressure-sensitive, hot-melt adhesives, so that the coating may be easily removed from an adhesive strip without disturbing the adhesive strip, while having high adhesion to the water-sensitive film of the flushable release liner/wiper combination. The coating formulation ensures that the flushable release liner/wiper combination peels at the surface of the release coating, not at the interface between the coating and water-sensitive base film of the flushable release liner/wiper combination.

In one embodiment of the present invention, the release coating of the flushable release liner/wiper combination is a polyalphaolefin having a melt viscosity of about 400 to about 8,000 cps at 190° C. Such polyalphaolefins include, but are not limited to, amorphous ethylene-propylene copolymers. Particularly suitable release materials are manufactured by the U.S. Rexene Company under the tradename REXTAC®. One REXTAC® resin, RTE32, is particularly suitable for the present invention. In a further embodiment, one or more REXTAC® resins are blended with a low molecular weight, highly branched hydrocarbon to reduce the tackiness of the release material coating. Desirably, the highly branched hydrocarbon has a number-average molecular weight ($M_n$) of less than about 2800. A particularly suitable low molecular weight, highly branched hydrocarbon, VYBAR® 253 ($M_n$=520), is manufactured by the Petrolite Corporation. Blends of REXTAC® and VYBAR® 253 provide good results as release coating materials. Desirably, the ratio of REXTAC® resin to VYBAR® 253 is from about 100/0 wt/wt to about 70/30 wt/wt. More desirably, the ratio of REXTAC® resin to VYBAR® 253 is from about 98/2 wt/wt to about 75/25 wt/wt. More desirably, the ratio of REXTAC® resin to VYBAR® 253 is from about 95/5 wt/wt to about 80/20 wt/wt. Particularly useful blends are RTE32/VYBAR® 253 (95/5 wt/wt) and RTE32/VYBAR® 253 (80/20 wt/wt).

The thickness of the release coating may vary greatly depending upon the end use of the flushable release liner/wiper combination and/or products containing the flushable release liner/wiper combination. However, film thickness should be minimized when possible to reduce product cost and to reduce the mechanical strength of the coating, particularly for flushable products, so that the coating will disperse due to the flushing forces of water on the coating. It should be noted that a suitable discontinuous release coating may have a thickness greater than a suitable continuous release coating. Desirably, the release coating thickness will be less than about 2.0 mil. (50.8 micrometers). More desirably, the release coating thickness will be less than about 0.5 mil. (12.7 micrometers). Most desirably, the release coating thickness will be less than about 0.1 mil. (2.5 micrometers). However, the coating should be thick enough to provide release characteristics along the film surface.

Water-sensitive films for use in the flushable release liner/wiper combination of the present invention include any water-sensitive film capable of withstanding the above-described coating processes. As used herein, the phrase "water-sensitive film" describes films, which lose integrity over time when in the presence of water and includes, but is not limited to, water-soluble films and water-dispersible films. Suitable polymers include, but are not limited to, polyalkylene oxides, such as polyethylene oxide (PEO) and ethylene oxide/propylene oxide copolymers, polymethacrylic acid, polymethacrylic acid copolymers, polyvinyl alcohol, poly(2-ethyl oxazoline), polyvinyl methyl ether, polyvinyl pyrrolidone/vinyl acetate copolymers, methyl cellulose, ethyl cellulose, hydroxypropyl cellulose, hydroxypropyl methyl cellulose, ethyl hydroxyethyl cellulose, methyl ether starch, poly (n-isopropyl acrylamide), poly N-vinyl caprolactam, polyvinyl methyl oxazolidone, poly (2-isopropyl-2-oxazoline), and poly (2,4-dimethyl-6-triazinyl ethylene).

The water-sensitive film component of the flushable release liner/wiper combination may also be made by combining various different types of water-sensitive film materials. Additionally, the water-sensitive film may be made entirely of water-sensitive polymeric material or may contain water-sensitive, as well as, water-insoluble materials so long as the film dissolves or disperses in water, such as in a conventional toilet or sink. The water-sensitive film component of the present invention may comprise up to about 70 weight percent water-insoluble material depending on a number of factors such as the type of water-insoluble material incorporated into the water-sensitive polymeric material, the morphology of the water-sensitive material/water-insoluble material blend, and the process for making the water-sensitive film. Suitable water-insoluble materials include, but are not limited to, polymeric materials and inorganic fillers, such as calcium carbonate or titanium dioxide. Inorganic fillers are particularly useful water-insoluble materials for incorporation into the water-sensitive films of the present invention in order to reduce film costs and provide aesthetic properties to the film such as color and texture. In some embodiments, it may be desirable to employ one or more additives into the water-sensitive film material including, but not limited to, compatibilizers, processing aids, surfactants, plasticizers, tackifiers, detackifiers, slip agents, and anti-microbial agents, as fabricating agents or as modifiers depending on the specific properties desired in the film and the final product.

Desirably, the water-sensitive film component of the present invention comprises a polyalkylene oxide film or a polyvinyl alcohol film. More desirably, the water-sensitive film component of the present invention comprises a polyethylene oxide film, an ethylene oxide/propylene oxide copolymer film or a polyvinyl alcohol film. In one embodiment of the present invention, the water-sensitive film component of the present invention comprises a polyethylene oxide film or a polyvinyl alcohol film. The polyethylene oxide film is the most desirable film for the transfer coating procedure, while the polyvinyl alcohol film is the most desirable film for the direct coating procedure. In a further embodiment of the present invention, the water-sensitive film of the flushable release liner/wiper combination comprises about 80 wt % polyethylene oxide, 15 wt % poly(ethylene-co-acrylic acid), and 5 wt % surfactant.

The thickness of the water-sensitive film of the flushable release liner/wiper combination may vary greatly depending upon the end use of the flushable release liner/wiper combination and/or products containing the flushable release liner/wiper combination. Film thickness should be minimized when possible to reduce product cost and to reduce the time necessary for the film to disperse, especially in the case of flushable products. Desirably, the water-sensitive film thickness will be less than about 2.0 mil (50.8 micrometers). More desirably, the water-sensitive film thickness will be from about 0.1 mil (2.5 micrometers) to about 1.4 mil (35.6 micrometers). Most desirably, the water-sensitive film thickness will be from about 0.1 mil (2.5 micrometers) to about 0.5 mil (12.7 micrometers).

The method of preparing the flushable release liner/wiper combination of the present invention further comprises attaching an absorbent fibrous material to a second surface of the water-sensitive film, opposite the release material coating. Any method known to those of ordinary skill in the art may be used to combine the water-sensitive film and the absorbent fibrous material of the flushable release liner/wiper combination. Suitable processes for attaching the absorbent fibrous material to the water-sensitive film include, but are not limited to, extrusion lamination, adhesive bonding and ultrasonic bonding. In one embodiment of the present invention, the absorbent fibrous material is extrusion laminated to the water-sensitive film as the water-sensitive film exits an extruder. In this process the absorbent fibrous material is brought into contact with a tacky surface of the water-sensitive film and is optionally passed through a nip point. The tackiness of the water-sensitive film (and the nip pressure) results in the adhesion of the absorbent fibrous material to the water-sensitive film surface. In an alternative process, the absorbent fibrous material is brought into contact with a surface of the water-sensitive film, which has been coated with an adhesive material. In this process, the choice of adhesive material and/or the discontinuity of the adhesive should be such that the adhesive material does not negatively impact the flushability of the flushable release liner/wiper combination. The adhesively bonded components may be optionally passed through a nip point as discussed above. The absorbent fibrous material of the flushable release liner/wiper combination of the present invention provides a wiping surface for the flushable release liner/wiper combination. Suitable absorbent fibrous materials include any fibrous material having sufficient strength and integrity for use in the above-described processes. Suitable absorbent fibrous materials include, but are not limited to, nonwoven fabrics. Desirably, the absorbent fibrous material is a nonwoven fabric comprising fibers having a fiber length of less than about 6 mm; however, fibers having a fiber length greater than 6 mm may be used as long as the fibers readily disperse under the flushing force of a toilet. The absorbent fibrous material may comprise synthetic polymeric fibers and/or natural fibers. In one embodiment of the present invention, the absorbent fibrous material of the flushable release liner/wiper combination comprises a coformed sheet containing about 40 to 50 wt % of a water-dispersible meltblown polyamide polymer and about 60 to 50 wt % of commercially available pulp (cellulose) fiber. Another suitable absorbent fibrous material for use in the present invention comprises a meltblown copolyester fiber, optionally containing up to 90 wt % of commercially available pulp (cellulose) fiber. A further suitable absorbent fibrous material for use in the present invention comprises an air-laid sheet containing water-sensitive or salt-sensitive binder fibers, optionally containing up to 90 wt % of commercially available pulp (cellulose) fiber.

With release characteristics and adhesion properties, the flushable release liner/wiper combination of the present invention finds applicability in a variety of articles. Specifically, the flushable release liner/wiper combination of the present invention is useful in connection with a variety of products, and especially absorbent products such as sanitary napkins, incontinence devices, diapers, dressings and the like. Although the flushable release liner/wiper combination of the present invention finds particular use in the above-mentioned products, the concept of a flushable release liner/wiper combination has potential for any other applications wherein a release liner and/or wiper is used.

Those skilled in the art will readily understand that the flushable release liner/wiper combination of the present invention may be advantageously employed in the preparation of a wide variety of products designed to contain at least one component having a release surface. Such products may comprise only the flushable release liner/wiper combination or may comprise the flushable release liner/wiper combination with one or more additional layers such as coatings, films, fabrics, etc. Although the flushable release liner/wiper combination of the present invention is particularly suited for release liner applications, the flushable release liner/wiper combination of the present invention may be advantageously employed in the preparation of a wide variety of consumer products other than release liners and release liner-containing products.

The present invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

Forming a Release Coating/Water-sensitive Film Laminate

A flushable release liner was made by the following process. A release coating comprising a blend of 30 wt % of a low molecular weight paraffin wax, VYBAR® 253 (Petrolite Polymers), and 70 wt % of a coating-grade polyalphaolefin, REXTAC® RTE32 (U.S. Rexene Company), was coated onto a base film comprising 80 wt % polyethylene oxide (POLYOX®, available from Union Carbide, Grade WSRN-80), 15 wt % poly(ethylene-co-acrylic acid) (PRIMACOR® 1410, available from Dow Chemical) and 5 wt % surfactant (TWEEN® 20, available from ICI Chemicals). The base film having the above composition, roughly 1.2 mil (30.5 micrometers) thick, was prepared at Huntsman Packaging (Chippawa Falls, Wis.) from resin pellets prepared at Planet Polymer (San Diego, Calif.). The blend was slot coated onto a high release paper and subsequently transferred to the base film under the following conditions: tank temperature, 315° F.; grid temperature, 324° F.; hose temperature, 340° F.; die temperature, 330° F.; and line speed, 24 ft/min. The blend was applied the base film to produce a final coating thickness of about 0.8 mil (20.3 micrometers).

The base Rexene resin itself showed good adhesion to the base film substrate, although slightly tacky. When blended with the VYBAR® additive, the adhesion with the base film substrate was improved while the tack of the coating was effectively suppressed.

Since Rexene resins themselves are used as a base component in many adhesives formulations, the resulting two-layer laminate was tested for adhesion to Rexene resins. The blend showed no adhesion to a coating of unblended RTE32. The blend also showed no adhesion to other Rexene coatings, such as a REXTAC® RT2330 coating.

The two-layer laminate readily broke up when held under gently flowing water from a sink tap. The resulting two-layer laminate displayed the key features required in a flushable release sheet.

EXAMPLE 2

Forming a Release Coating/Water-sensitive Film Laminate

Release coating material, REXTAC® RT2315, was coated on a high release paper, using a 40 mesh screen, and subsequently transferred to a base film identical to the base film used in Example 1 under the following conditions: tank temperature, 315° F.; grid temperature, 324° F.; hose temperature, 340° F.; die temperature, 330° F.; screen speed, 35 ft/min.; and line speed, 24 ft/min. Higher line speed facilitated the spreading of dots because of less temperature drop before the nip at pressure. At a line speed of 25 ft/min., coalescence of the dots started to occur. The average space between dots was about 0.1 mm on the release paper and about 0.05 mm on the base film. The dot spacing was reduced by increasing the nip pressure.

The effect of mismatching of the speeds of the screen and the paper was also studied. When the screen was running at higher speed than the paper, flatter dots with less space between them were seen, but coalescence was limited. When the screen speed was slightly less than that of the paper, part of the dot was pulled off as a crescent-shaped wing on one side of the dot, again with little coalescence. The film dispersed readily in tap water.

EXAMPLE 3

Forming a Release Coating/Water-sensitive Film Laminate

Release coating material, REXTAC® RT2535, was initially coated on a high release paper, using a 40 mesh screen, and subsequently transferred to a base film identical to the base film used in Example 1 under the following conditions: tank temperature, 330° F.; grid temperature, 340° F.; hose temperature, 345° F.; die temperature, 350° F.; screen speed, 35 ft/min.; and line speed, 24 ft/min. The dots were well separated; the average distance between dots was about 0.25 mm. The nip pressure had a profound effect on dot spreading. When the nip pressure was more than doubled, the average space between the dots was reduced to about 0.1 mm on the base film, and more coalescence was observed. Increasing coating temperatures to as much as 375° F. and mismatching the coating speed showed no significant influence on the dot spacing. The film dispersed readily in tap water.

EXAMPLE 4

Forming a Release Coating/Water-sensitive Film Laminate

To increase spreading capacity and to reduce the tackiness of the coating, 5 wt % of a low molecular weight highly branched hydrocarbon, VYBAR® 253, was added to the RT2330 resin. The blend was coated on a release paper and subsequently transferred to a base film identical to the base film used in Example 1 under the following conditions: tank temperature, 335° F.; grid temperature, 345° F.; hose temperature, 345° F.; die temperature, 354° F.; screen speed, 35 ft/min.; and line speed, 24 ft/min. The dots were elongated and substantial coalescence occurred. The average space between dots was about 0.2 mm on the release paper and about 0.1 mm on the base film. The film dispersed readily in tap water.

To further reduce the gap between dots, a 50 mesh screen, which has less space between holes, was used. The dots produced with the 50 mesh screen were smaller and did not coalesce. An increased paper speed of 25 ft/min., while maintaining the screen speed at 35 ft/min., resulted in some pulling of dots, but no improvement in coalescence of dots. An increase in all the temperatures by 10 degrees showed no difference in dot coalescence.

EXAMPLE 5

Forming a Release Coating/Water-sensitive Film Laminate

A blend comprising 80 wt % release coating material REXTAC® RT2730 and 20 wt % VYBAR® 253 was coated on a high release paper, using a 40 mesh screen, and subsequently transferred to a base film identical to the base film used in Example 1 under the following conditions: tank temperature, 301° F.; grid temperature, 303° F.; hose temperature, 309° F.; die temperature, 312° F.; screen speed, 35 ft/min.; and line speed, 25 ft/min. Significantly lower processing temperatures were used because of the relatively large weight percentage of VYBAR® 253. The blend had good spreading capability. The dots appeared flatter, and more coalescence was observed. The average distance between dots was about 0.1 mm. The coated base film dispersed readily when exposed to a large body of water.

EXAMPLE 6

Forming Wiper Combination Laminates

A coated water-sensitive film and a coformed sheet comprising 40 wt % of water-dispersible meltblown polyamide fibers (made from a polymer, Code NP-2068, supplied by H.B. Fuller Company of St. Paul, Minn.) and 60 wt % Weyerhauser cellulose fiber pulp are extrusion laminated to form a coated water-sensitive film/wiper combination laminate.

Having thus described the invention, numerous changes and modifications thereof will be readily apparent to those having ordinary skill in the art, without departing from the spirit or scope of the invention.

What is claimed is:

1. A flushable laminate having release characteristics, said laminate comprising:
    a water-sensitive film having a first surface and a second surface, the second surface being opposite to the first surface;
    a release coating on the first surface of the water-sensitive film, wherein the coating adheres to the water-sensitive film and provides release characteristics to the laminate; and
    an absorbent fibrous material on the second surface of the water-sensitive film.

2. The flushable laminate of claim 1, wherein the water-sensitive film comprises polyethylene oxide, ethylene oxide/propylene oxide copolymers, polymethacrylic acid, polymethacrylic acid copolymers, polyvinyl alcohol, poly(2-ethyl oxazoline), polyvinyl methyl ether, polyvinyl pyrrolidone/vinyl acetate copolymers, methyl cellulose, ethyl cellulose, hydroxypropyl cellulose, hydroxypropyl methyl cellulose, ethyl hydroxyethyl cellulose, methyl ether starch, poly (n-isopropyl acrylamide), poly N-vinyl caprolactam, polyvinyl methyl oxazolidone, poly (2-isopropyl-2-oxazoline), poly (2,4-dimethyl-6-triazinyl ethylene) or a combination thereof.

3. The flushable laminate of claim 2, wherein the water-sensitive film comprises polyethylene oxide, ethylene oxide/propylene oxide, polyvinyl alcohol or a combination thereof.

4. The flushable laminate of claim 1, wherein the release coating comprises a polyolefin, a fluoropolymer, a silicone or a combination thereof.

5. The flushable laminate of claim 4, wherein the release coating comprises a continuous coating.

6. The flushable laminate of claim 4, wherein the release coating comprises a discontinuous coating.

7. The flushable laminate of claim 3, wherein the water-sensitive film comprises polyethylene oxide in combination with poly(ethylene-co-acrylic acid).

8. The flushable laminate of claim 1, wherein the absorbent fibrous material comprises a nonwoven fabric.

9. The flushable laminate of claim 8, wherein the absorbent fibrous material comprises a nonwoven fabric selected from the group consisting of (a) a coformed fabric containing about 10 to 90 wt % meltblown polyamide fibers and about 90 to 10 wt % cellulose pulp fibers, (b) a nonwoven fabric containing about 10 to 90 wt % meltblown copolyester fibers and about 90 to 10 wt % cellulose pulp fibers, and (c) an air-laid fabric containing 10 to 90 wt % water-sensitive or salt-sensitive binder fibers and about 90 to 10 wt % cellulose pulp fibers.

10. The flushable laminate of claim 1, wherein the water-sensitive film has a thickness of less than about 1.0 mil (25.4 micrometers) and the release coating has a thickness of less than about 0.5 mil (12.7 micrometers).

11. A flushable release liner/wiper combination comprising:
    a water-sensitive film;
    a release coating on a first surface of the water-sensitive film, wherein the coating adheres to the water-sensitive film and provides release characteristics to the release liner/wiper combination; and
    an absorbent fibrous material on a second surface of to the water-sensitive film opposite the first surface.

12. The flushable release liner/wiper combination of claim 11, wherein the water-sensitive film comprises polyethylene oxide, ethylene oxide/propylene oxide copolymers, polymethacrylic acid, polymethacrylic acid copolymers, polyvinyl alcohol, poly(2-ethyl oxazoline), polyvinyl methyl ether, polyvinyl pyrrolidone/vinyl acetate copolymers, methyl cellulose, ethyl cellulose, hydroxypropyl cellulose, hydroxypropyl methyl cellulose, ethyl hydroxyethyl cellulose, methyl ether starch, poly (n-isopropyl acrylamide), poly N-vinyl caprolactam, polyvinyl methyl oxazolidone, poly (2-isopropyl-2-oxazoline), poly (2,4-dimethyl-6-triazinyl ethylene) or a combination thereof.

13. The flushable release liner/wiper combination of claim 12, wherein the water-sensitive film comprises polyethylene oxide in combination with poly(ethylene-co-acrylic acid).

14. The flushable release liner/wiper combination of claim 11, wherein the release coating comprises a continuous coating.

15. The flushable release liner/wiper combination of claim 11, wherein the release coating comprises a discontinuous coating.

16. The flushable release liner/wiper combination of claim 11, wherein the absorbent fibrous material comprises a nonwoven fabric.

17. A product comprising:
    a flushable laminate, wherein the flushable laminate comprises:
        a water-sensitive film;
        a release coating on a surface of the water-sensitive film, wherein the coating adheres to the water-sensitive film and provides release characteristics to the laminate; and
        an absorbent fibrous material on a second surface of the water-sensitive film opposite the first surface; and
    at least one additional layer adhered to the release coating of the laminate.

18. The product of claim 17, wherein the product comprises a feminine napkin, a panty liner, an incontinence device, a bandage or a diaper.

* * * * *